(12) United States Patent
Jordan

(10) Patent No.: US 11,904,018 B2
(45) Date of Patent: Feb. 20, 2024

(54) SYSTEMS AND METHODS FOR DELIVERY OF EXOSOMES VIA MRI

(71) Applicant: Synaptec Research, Inc., Santa Monica, CA (US)

(72) Inventor: Sheldon Jordan, Santa Monica, CA (US)

(73) Assignee: Synaptec Network, Inc., Santa Monica, CA (US)

( * ) Notice: Subject to any disclaimer, the term of this patent is extended or adjusted under 35 U.S.C. 154(b) by 43 days.

(21) Appl. No.: 17/182,693

(22) Filed: Feb. 23, 2021

(65) Prior Publication Data

US 2021/0260189 A1   Aug. 26, 2021

Related U.S. Application Data

(60) Provisional application No. 62/980,875, filed on Feb. 24, 2020.

(51) Int. Cl.
*A61K 41/00* (2020.01)
*A61N 2/00* (2006.01)
*A61M 37/00* (2006.01)

(52) U.S. Cl.
CPC .......... *A61K 41/0052* (2013.01); *A61N 2/002* (2013.01); *A61M 2037/0007* (2013.01)

(58) Field of Classification Search
CPC ....... A61B 5/00; A61B 5/0033; A61B 5/0036; A61K 41/00; A61K 41/0028; A61K 41/0052; A61N 2/00; A61N 2/004; A61N 2/002; A61M 2037/0007; A61M 37/00; A61M 2205/057; A61M 2210/0693
See application file for complete search history.

(56) References Cited

U.S. PATENT DOCUMENTS

| 5,690,109 | A  | 11/1997 | Govind et al. |
| 9,844,679 | B2 | 12/2017 | Nayfach-Battilana |
| 2005/0090732 | A1 | 4/2005 | Ivkov |

(Continued)

FOREIGN PATENT DOCUMENTS

| WO | WO2011113140 A1 | 9/2011 |
| WO | 2015200576 A1 | 12/2015 |

OTHER PUBLICATIONS

International Search Report and Written Opinion, PCT application No. PCT/US2021/019242, dated Jun. 11, 2021.

(Continued)

*Primary Examiner* — Jason E Flick
(74) *Attorney, Agent, or Firm* — Fish IP Law, LLP

(57) ABSTRACT

Systems, methods, and devices for administering, improving administration, or enabling the selective delivery of an agent to a target portion of a tissue are disclosed. An MRI device, at least high strength (e.g., at least 3 T), more preferably ultra high strength (e.g., at least 10 T) is directed at and applied to a target portion of a tissue, preferably brain tissue. A magnetic field is applied to the target portion of the tissue, selectively increasing local temperature and not impacting core temperature. The agent, preferably exosome carrying a therapeutic, is administered to the patient, and the agent is selectively delivered to the target portion of the tissue. Magnetic fields are optionally applied to the target portion before, during, or after administering the agent, or combinations thereof.

19 Claims, 3 Drawing Sheets

(56) References Cited

U.S. PATENT DOCUMENTS

| | | | |
|---|---|---|---|
| 2007/0164250 A1 | 7/2007 | Hamad-Schifferli et al. | |
| 2010/0125191 A1 | 5/2010 | Sahin | |
| 2015/0209566 A1* | 7/2015 | Peyman | A61B 5/0036 |
| | | | 604/20 |
| 2018/0292479 A1* | 10/2018 | Barbic | G01R 33/5601 |
| 2021/0275440 A1* | 9/2021 | Mohapatra | A61K 9/1682 |

OTHER PUBLICATIONS

Staruch, Robert Michael. "Hyperthermia Mediated Drug Delivery using Thermosensitive Liposomes and MRI-Controlled Focused Ultrasound," A thesis submitted in conformity with the requirements for the degree of Doctor of Philosophy Department of Medical Biophysics University of Toronto. 2013. 175 pages.

Van den Brink, Johan S. "Thermal Effects Associated with RF Exposures in Diagnostic MRI: Overview of Existing and Emerging Concepts of Protection," Concepts in Magnetic Resonance Part B vol. 2019, Article ID 9618680, 17 pages.

* cited by examiner

SYSTEMS AND METHODS FOR DELIVERY OF EXOSOMES VIA MRI

This application claims priority to U.S. provisional application No. 62/980,875, filed Feb. 24, 2020, the disclosure of which is incorporated herein by reference.

FIELD OF THE INVENTION

The field of the invention is methods, systems, kits, and devices related to improving delivery of therapeutics to patients.

BACKGROUND

The background description includes information that may be useful in understanding the present invention. It is not an admission that any of the information provided herein is prior art or relevant to the presently claimed invention, or that any publication specifically or implicitly referenced is prior art.

When developing possible therapies for conditions, diseases, or disorders that are localized to a tissue or best treated via a particular tissue, a key obstacle is how the therapy will be delivered or administered to the therapeutic region of interest in the tissue. While surgical administration is generally an option, in many cases it is unfavorable as it increases risk of infection or harm to a patient. Methods of indirect administration are also known, such as administering therapeutic agents to the blood stream, agitating or stimulating agents in the blood stream, or agitating or stimulating portions of a tissue with acoustic or other energy waves. For example, *Thesis: Hyperthermia Mediated Drug Delivery Using Thermosensitive Liposomes And Mri-Controlled Focused Ultrasound* by Staruch (Department of Medical Biophysics, University of Toronto 2013) teaches using MRI to guide ultrasound to selectively target and heat portions of the patient's body, which causes thermosensitive liposomes to release drugs at that region. Similarly, US 2005/0090732 to Ivkov et al., teaches applying MRI to a particle at a location in the patient's body to oscillate the particle, thereby generating heat at the targeted region. Such particles include a selective ligand that can target specific markers or conditions in the patient's tissue or cells.

All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

However, *Thermal Effects Associated with RF Exposures in Diagnostic MRI: Overview of Existing and Emerging Concepts of Protection* by van den Brink (Hindawi, Concepts in Magnetic Resonance Part B, Vol. 2019, Article ID 9618680) teaches long duration MRI or ultra/high field strength MRI increases the temperature in the patient's body, both local to the applied region and the patient's core temperature. van den Brink cautions of the damage of diagnostic MRI or RF hyperthermia on the body, and dissuades use of the practice outside of established guidelines.

Thus, there remains a need for systems, methods, and devices for to safely improve or facilitate delivery of therapeutic agents to a target tissue by targeted application of high or ultra high field strength MRI.

SUMMARY OF THE INVENTION

The inventive subject matter provides apparatus, systems, and methods for improving, facilitating, or enabling delivery (preferably selective delivery) of an agent to a target portion of a tissue, preferably in a human patient. A magnetic resonance imaging (MRI) device is directed toward the target portion of the tissue to emit a magnetic field targeted at the portion of the tissue (e.g., brain tissue). The MRI device is then used to apply a high strength magnetic field (e.g., no less than 3 Tesla (T)) toward the target portion of the tissue. The agent is administered to the tissue and selectively delivered to the target portion of the tissue. In some embodiments, the agent is administered (e.g., injected) to the patient before applying the magnetic field, though it is contemplated that the agent be administered substantially concurrent with applying the magnetic field, or after applying the magnetic field.

Methods of improving delivery (preferably selective) of an agent to a target portion of a tissue are further contemplated. An MRI device is directed toward the target portion of the tissue and used to apply a high strength magnetic field toward the target portion of the tissue. The high strength magnetic field acts to increase tissue temperature local to the target portion of the tissue (e.g., between 0.5° C. and 5° C.), thereby improving delivery of the agent. The agent is typically an exosome, preferably carrying a therapeutic agent, and preferably administered to the tissue after the step of using the MRI device. High strength magnetic fields are generally at least 3 T.

Methods of enabling delivery (preferably selective) of an agent to a target portion of a tissue are also contemplated. An MRI is directed device toward the target portion of the tissue and used to apply a high strength magnetic field (e.g., at least 3 T) toward the target portion of the tissue. The high strength magnetic field increases temperature local to the target portion of the tissue, and does not substantially (e.g., more than 1° C., 2° C., 3° C., or more than 4° C.) increase the patient's core temperature. The application of the magnetic field and increase of temperature in the proximal tissue enables delivery of the agent.

Various objects, features, aspects and advantages of the inventive subject matter will become more apparent from the following detailed description of preferred embodiments, along with the accompanying drawing figures in which like numerals represent like components.

DETAILED DESCRIPTION

Figure 1:
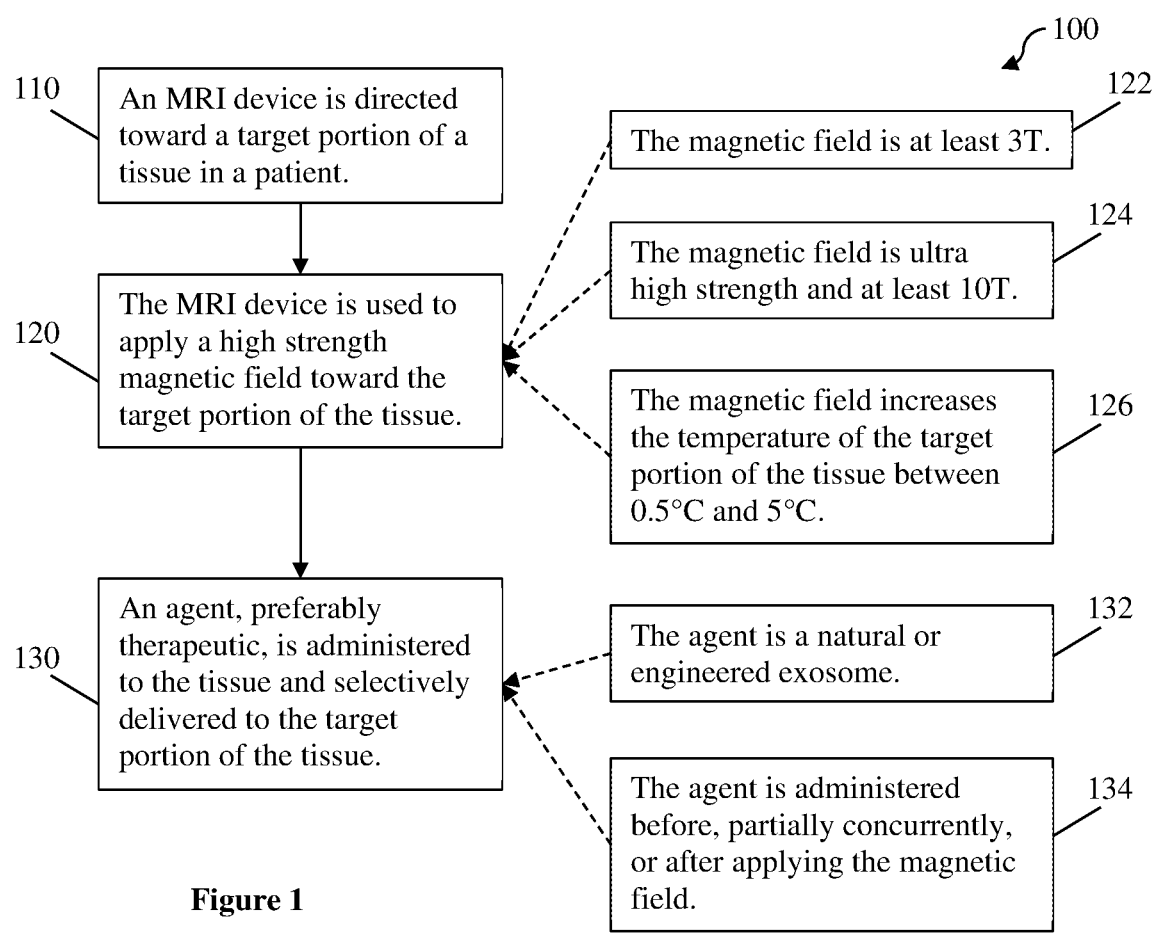
FIG. 1 depicts a flow chart of a method of the inventive subject matter.

The inventive subject matter provides apparatus, systems, and methods for improving, facilitating, or enabling delivery (preferably selective delivery) of an agent to a target portion of a tissue, preferably in a human patient. A magnetic resonance imaging (MRI) device is directed toward the target portion of the tissue to emit a magnetic field targeted at the portion of the tissue (e.g., brain tissue). The MRI device is then used to apply a high strength magnetic field (e.g., no less than 3 Tesla (T)) toward the target portion of the tissue. The agent is administered to the tissue and selectively delivered to the target portion of the tissue.

In some embodiments, the agent is administered (e.g., injected) to the patient before applying the magnetic field, though it is contemplated that the agent be administered substantially concurrent with applying the magnetic field, or after applying the magnetic field, or combinations thereof. For example, the magnetic field is applied to the targeted tissue before administering the agent, the magnetic field is then removed, and after a duration (e.g., 30 s, 1, 2, 3, 4, 5, 10, or 30 min, etc.) the magnetic field is reapplied to further aid in administering or delivering the agent to the target tissue. The agent can also be resident proximal to the target portion of the tissue during the step of using the MRI device, for example via direct injection to the target portion of the tissue. In preferred embodiments, the agent (preferably therapeutic) is administered after, and temporally proximal, to the step of applying the high strength magnetic field, for example within 0.1 s, 1 s, 2 s, 3 s, 4 s, 5 s, 10 s, or 30 s.

The agent is typically natural or engineered, for example one of a large molecule, an injectable therapeutic, a cellular component, a tissue component, a lipid vesicle, a nanoparticle, an exosome, a lipid bilayer, a pharmaceutical, a stem cell, or combinations or packaged combinations (e.g., pharmaceutical in an exosome) thereof. In preferred embodiments, the agent has a therapeutic affect on the targeted tissue, either directly or indirectly. In preferred embodiments, the agent is an exosome, optionally carrying a therapeutic agent.

The high strength magnetic field is typically at least 3 T, and in some embodiments the magnetic field is an ultra high strength magnetic field, for example at least 10 T. It is contemplated that the magnetic field be between 3 T and 7 T, 7 T and 10 T, 10 T and 22 T, or more than 22 T (e.g., 22 T to 30 T, etc.). Applying the high strength (or ultra high strength) magnetic field increases the temperature of the target portion of the tissue, which in turn improves delivery of the agent to the target portion of the tissue. The temperature increase is typically between 0.5° C. and 5° C., 3° C. and 8° C., or 5° C. and 10° C. In preferred embodiments, the temperature increase is localized to the target portion of the tissue, and does not raise the temperature in distal tissue or increase the core temperature of the patient. It is also contemplated that applying the magnetic field relaxes tissues or membranes in the target tissue, further improving delivery of the agent to the target portion of the tissue.

Further, it is contemplated that ultra high strength and high strength MRI can be applied in a coordinated fashion, for example ultra high strength for a duration (e.g. 20 s, 40 s, 1, 2, 3, or 5 min, etc.) before administering the agent, high strength is applied after administration, and ultra high strength is again applied a period after administration of the agent (e.g., 1, 2, 3, 4, 5, 10, or 20 min etc.). It is also contemplated that high strength MRI can be applied before, during, and after administration of the agent, with ultra high strength applied periodically (e.g., every 10, 20, or 40 sec, 1, 2, or 3 min, etc.) throughout the pre-administration, administration, or post-administration process, or vice versa.

Methods of improving delivery (preferably selective) of an agent to a target portion of a tissue are further contemplated. An MRI device is directed toward the target portion of the tissue and used to apply a high strength magnetic field toward the target portion of the tissue. The high strength magnetic field acts to increase tissue temperature local to the target portion of the tissue (e.g., between 0.5° C. and 5° C.), thereby improving delivery of the agent. The agent is typically an exosome, preferably carrying a therapeutic agent, and preferably administered to the tissue after the step of using the MRI device. High strength magnetic fields are generally at least 3 T. In some embodiments, the magnetic field is an ultra high strength magnetic field, for example at least 10 T.

Methods of enabling delivery (preferably selective) of an agent to a target portion of a tissue are also contemplated. An MRI device is directed toward the target portion of the tissue and used to apply a high strength magnetic field (e.g., at least 3 T) toward the target portion of the tissue, in some embodiments in concert with an ultra high strength magnetic field. The high strength magnetic field increases temperature local to the target portion of the tissue, and does not substantially (e.g., more than 1° C., 2° C., 3° C., or more than 4° C.) increase the patient's core temperature. The application of the magnetic field and increase of temperature in the proximal tissue enables delivery of the agent. In preferred embodiments, such agents are natural or engineered, and can be one or more of a large molecule, an injectable therapeutic, a cellular component, a tissue component, a lipid vesicle, a nanoparticle, an exosome, a pharmaceutical, a stem cell, or combinations or packaged combinations thereof.

In some embodiments, the magnetic field is applied in pulses, for example no more than 0.1 Hz, 1 Hz, 2 Hz, 5 Hz, 10 Hz, 100 Hz, 1 MHz, 1 GHz, or no more than 1 THz. The magnetic field can also be applied continuously. It is contemplated that pulses of magnetic field are applied to selectively increase temperature of the tissue at the targeted region, to prevent overheating of the target tissue, and to avoid increasing temperature of distal tissue or core temperature of the patient.

FIG. 1 depicts flowchart 100 for a method of selectively delivering an agent to a target portion of a tissue. Flowchart 100 includes required steps 110, 120, and 130, as well as preferred steps 122, 124, 126, 132, and 134, which are conducted as described. In some embodiments, one or more of preferred steps 122, 124, 126, 132, and 134 are used.

Figure 2:
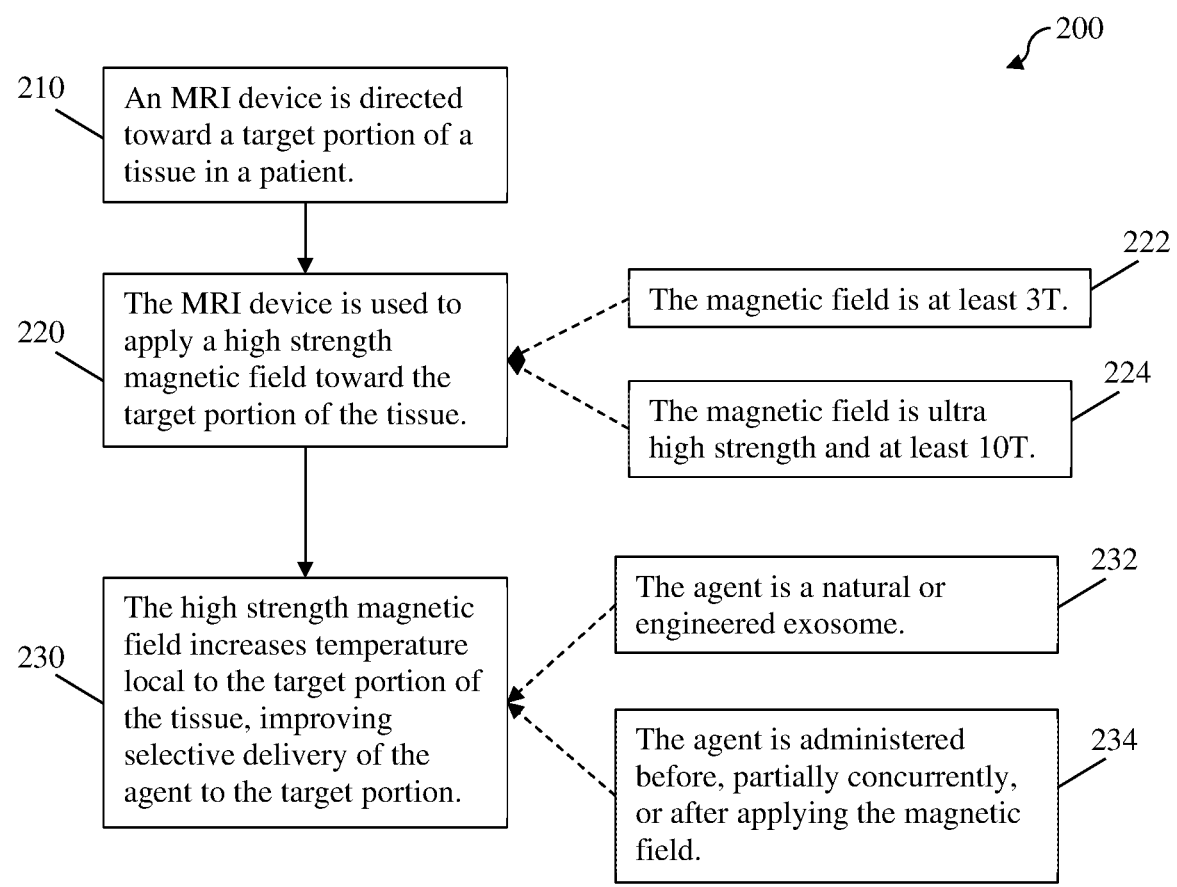
FIG. 2 depicts another flow chart of a method of the inventive subject matter.

FIG. 2 depicts flowchart 200 for a method of improving selective delivery of an agent to a target portion of a tissue. Flowchart 200 includes required steps 210, 220, and 230, as well as preferred steps 222, 224, 232, and 234, which are conducted as described. In some embodiments, one or more of preferred steps 222, 224, 232, and 234 are used.

Figure 3:
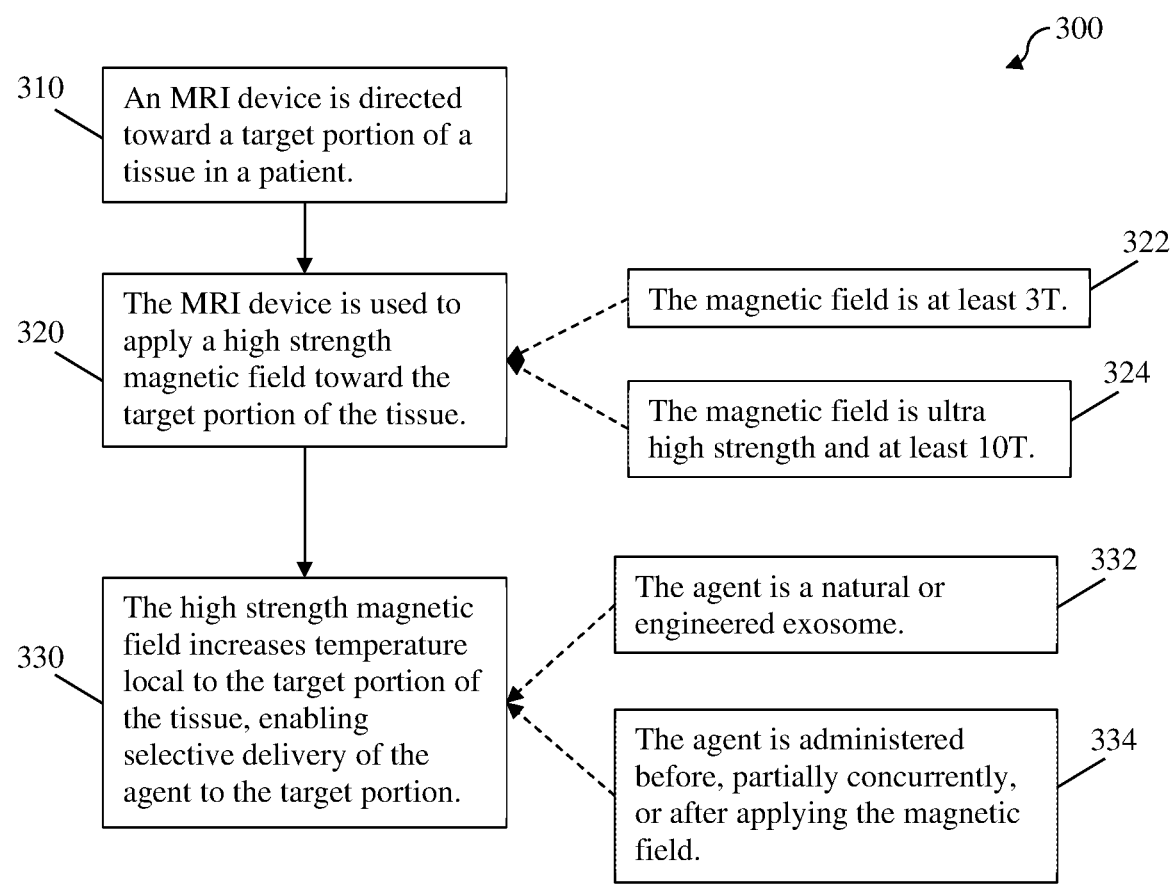
FIG. 3 depicts yet another flow chart of a method of the inventive subject matter.

FIG. 3 depicts flowchart 300 for a method of enabling selective delivery of an agent to a target portion of a tissue. Flowchart 300 includes required steps 310, 320, and 330, as well as preferred steps 322, 324, 332, and 334, which are conducted as described. In some embodiments, one or more of preferred steps 322, 324, 332, and 334 are used.

The following description includes information that may be useful in understanding the present invention. It is not an admission that any of the information provided herein is prior art, necessary, or relevant to the presently claimed invention, or that any publication specifically or implicitly referenced is prior art.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of selectively delivering an exosome carrying a therapeutic agent to a target portion of a tissue, comprising:
   directing a magnetic resonance imaging (MRI) device toward the target portion of the tissue;
   using the MRI device to apply a magnetic field toward the target portion of the tissue; and
   administering the exosome carrying the therapeutic agent to the tissue after the MRI device is used to apply the magnetic field.

2. The method of claim 1, wherein the magnetic field is at least 3 Tesla (T).

3. The method of claim 1, further comprising using the MRI device to apply a second magnetic field toward the target portion of the tissue.

4. The method of claim 1, wherein the magnetic field is at least 10 T.

5. The method of claim 1, wherein applying the magnetic field increases the temperature of the target portion of the tissue.

6. The method of claim 5, wherein the temperature increase is between 0.5° C. and 5° C.

7. The method of claim 5, wherein the temperature increase is localized to the target portion of the tissue.

8. The method of claim 1, wherein the exosome carrying the therapeutic agent is resident proximal to the target portion of the tissue during the step of using the MRI device.

9. The method of claim 1, wherein the tissue is brain tissue.

10. A method of improving selective delivery of an agent to a target portion of a tissue of a patient, comprising:
    directing a MRI device toward the target portion of the tissue;
    using, while the agent is outside the patient, the MRI device to apply a magnetic field toward the target portion of the tissue, wherein the magnetic field increases temperature local to the target portion of the tissue, thereby improving selective delivery of the agent to the target portion; and
    administering, after applying the magnetic field, the agent into the patient.

11. The method of claim 10, wherein the agent is an exosome.

12. The method of claim 11, wherein the agent is an exosome carrying a therapeutic agent.

13. The method of claim 10, wherein the magnetic field is at least 3 T.

14. The method of claim 10, wherein the magnetic field is at least 10 T.

15. The method of claim 10, wherein the temperature increase is between 0.5° C. and 5° C.

16. The method of claim 10, wherein the agent is resident proximal to the target portion of the tissue during the step of using the MRI device.

17. The method of claim 10, wherein the tissue is brain tissue.

18. A method of enabling selective delivery of an agent to a target portion of a tissue of a patient, comprising:
    directing a MRI device toward the target portion of the tissue;
    using the MRI device to apply a magnetic field toward the target portion of the tissue, wherein the magnetic field increases temperature local to the target portion of the tissue, thereby enabling selective delivery of the agent to the target portion; and
    injecting the agent into the patient at least partially concurrently while applying the magnetic field.

19. The method of claim 18, wherein the agent is natural or engineered and selected from the group consisting of a large molecule, an injectable therapeutic, a cellular component, a tissue component, a lipid vesicle, a nanoparticle, an exosome, a pharmaceutical, or a stem cell.

\* \* \* \* \*